United States Patent
Davis et al.

(10) Patent No.: US 10,213,326 B2
(45) Date of Patent: Feb. 26, 2019

(54) STENT GRAFT WITH FENESTRATION

(71) Applicant: Cook Medical Technologies LLC, Bloomington, IN (US)

(72) Inventors: Brandon Davis, West Lafayette, IN (US); Matthew S. Huser, West Lafayette, IN (US); Jarin Kratzberg, Lafayette, IN (US); Kimberly Ringenberger, Zionsville, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 0 days.

(21) Appl. No.: 14/830,399

(22) Filed: Aug. 19, 2015

(65) Prior Publication Data

US 2017/0049588 A1 Feb. 23, 2017

(51) Int. Cl.
*A61F 2/856* (2013.01)
*A61F 2/07* (2013.01)
*A61F 2/06* (2013.01)

(52) U.S. Cl.
CPC ............. *A61F 2/856* (2013.01); *A61F 2/07* (2013.01); *A61F 2002/061* (2013.01); *A61F 2210/0071* (2013.01); *A61F 2230/0069* (2013.01)

(58) Field of Classification Search
CPC .... A61F 2/06; A61F 2/07; A61F 2/856; A61F 2002/0616; A61F 2210/0071
See application file for complete search history.

(56) References Cited

U.S. PATENT DOCUMENTS

| | | | |
|---|---|---|---|
| 5,282,848 A | 2/1994 | Schmitt | |
| 7,645,298 B2 | 1/2010 | Hartley et al. | |
| 2007/0055356 A1 | 3/2007 | Eidenschink | |
| 2010/0063576 A1 | 3/2010 | Schaeffer et al. | |
| 2010/0268327 A1 | 10/2010 | Bruszewski et al. | |
| 2012/0046728 A1 | 2/2012 | Huser et al. | |
| 2013/0116773 A1* | 5/2013 | Roeder ............. | A61F 2/07 623/1.15 |

FOREIGN PATENT DOCUMENTS

WO 2005-034809 A1 4/2005
WO 2010-024849 A1 3/2010

OTHER PUBLICATIONS

European Search Report for EP 16275103.6, Cook Medical Technologies LLC, dated Nov. 7, 2016.

* cited by examiner

*Primary Examiner* — Dinah Baria
(74) *Attorney, Agent, or Firm* — Richard J. Godlewski

(57) ABSTRACT

An endovascular prosthesis and method of constructing a prosthesis device for implantation into the lumen of a body vessel. The endovascular prosthesis includes a fenestration in the device surrounded by an inner edge, and the inner edge further surrounded by an outer edge of larger diameter. A shaped protrusion of semi-rigid graft material spans the distance between the inner edge and the outer edge connecting the two edges. The shape protrusion has a surface area larger than the plane of the tubular body between the edges and therefore will have excess material. This excess material allows the inner edge and the fenestration to move within the circumference of the outer edge. The shaped protrusion may also form a semi-rigid dome.

19 Claims, 8 Drawing Sheets

STENT GRAFT WITH FENESTRATION

FIELD OF THE INVENTION

This invention relates to a stent graft with fenestrations wherein the fenestrations are surrounded by a thermoset graft material. The invention also relates to the method of construction which includes the setting of the graft material to form the fenestrations on a stent graft.

BACKGROUND OF THE INVENTION

An aneurysm develops when the repeated shock of blood flowing through a vessel causes a weakened vessel wall to bulge. Untreated, an aneurysm can eventually rupture causing bleeding and leading to hypovolemic shock and eventually death. Fortunately, stent grafts can be used to bypass the damaged portion of the blood vessel. The stent graft is placed on an introducer and the combined assembly is introduced into the patient percutaneously. The assembly is advanced through a patient's vasculature to the treatment site, and then the stent graft is deployed at the site of the aneurysm.

The size of a patient's vasculature and the size of the assembly can limit options for treatment. For example, potentially effective stent graft and introducer systems may be too large to fit into and traverse smaller vasculature safely. Thus there is an advantage to reducing the compressed size of the stent graft and the introducer. One method of reducing stent graft size is to reduce the features on the stent graft. This has the additional advantage of eliminating unnecessary manufacturing steps.

In addition, accurate and effective placement of the stent graft in vasculature can be tricky. For example, a stent graft may need to be placed such that its ends seal against the walls of the blood vessel above and below the aneurysm. When placed correctly, blood pressure is redirected against the walls of the stent graft instead of the weakened vessel wall. This decreases the likelihood that the aneurysm will enlarge or rupture.

Where the aneurysmal area includes branch vessels, it may be desirable to preserve the natural path of blood flow from the affected vessel to its side branches to ensure continued perfusion of peripheral body systems. One method of preserving blood flow to peripheral vessels utilizes connecting stents deployed through fenestrations in the stent graft's side wall. This method fluidly links the stent graft lumen to the side branch lumen via the connecting stent lumen. For example, a stent graft placed in the abdominal aorta may block the renal arteries and impair the function of the kidneys unless connecting stents can be deployed in the stent graft wall fenestrations that abut the ostia of the renal arteries.

A problem arises when the unique proportions of a patient's vessel do not match the proportions of a manufactured stent graft. This can occur when the aneurysm is located in a vessel such that the ostium of a branch vessel will not align with the manufactured stent graft fenestration when deployed.

For example, a stent graft may have a fenestration which is centered at 20 mm from its end. However, a target vessel may have a side branch centered at 25 mm from the end when the stent graft is deployed. Thus, the deployed stent graft will partially occlude the side branch. The difficulty of cannulating the side branch and deploying a connecting stent is increased, and even when the connecting stent is successfully deployed, the connecting stent may be pinched, restricting blood flow to the side branch.

This problem is further compounded as the number of fenestrations and target side branches increase. For example, two fenestrations on a stent graft may be 15 mm from each other, but the side branches of the vessel are 20 mm from each other. Deploying the stent graft will result in partial occlusion of both side branches. In the alternative, one side branch can be fully aligned, but at the cost of further occlusion of the remaining side branch.

Prior attempts at addressing this problem use various methods of making the fenestrations adjustable. For example, a reinforced dome around the fenestration allows the connecting stent to tilt and adjust its angle. Huser (US Patent App 20120046728). The use of corrugated graft material near the fenestration provides some flexibility to the fenestration Hartley (U.S. Pat. No. 7,645,298).

There is a need in the art for an improved adjustable fenestration that can safely and effectively link a stent graft lumen to a side branch lumen despite imperfect matching of the fenestration and the side branch.

SUMMARY OF THE INVENTION

The present disclosure describes a stent graft capable of treating diseased vessels and cannulating their side branch vessels and a method of constructing the stent graft. Although introduced in the background of treating aneurysms caused by weakened vessel walls, the invention is not limited to such and may be used in any situation where traversing a section of a body vessel or cannulating a branch vessel would be useful.

The invention comprises an endovascular prosthesis having a tubular body having a wall and comprising a graft material. The tubular body preferably comprises a flexible graft material. A shaped protrusion of graft material extends from the wall. The shaped protrusion preferably comprises a semi-rigid material, enabling it to hold its shape in the absence of external manipulation. It is more preferable that the shaped protrusion comprise a thermoset material. The shaped protrusion has an inner edge within an outer edge and has no stents or other structures between the edges. A fenestration has fluid communication through the wall and is disposed within the inner edge in the shaped protrusion.

The shaped protrusion has a transverse length and may curve along its transverse length, taking an undulating or domed shape.

The shaped protrusion comprises excess graft material. The surface area of the shaped protrusion is greater than the area of an annular curvilinear plane along the wall of the tubular body, delineated by the outer edge and inner edge when in a position coincident with the circumference of the wall.

The inner edge and the outer edge may be concentric or eccentric. The outer edge and the inner edge may be coincident with the circumference of the tubular body. If so, the edges align with the circumference of the tubular body in a coplanar manner.

The shaped protrusion preferably remains outside of the plane of the tubular body or in an alternate embodiment is at least within the plane of the tubular body as minimally as possible.

The shaped protrusion may extend from the wall to form a dome.

In one embodiment where the outer edge and the inner edge are coincident with the circumference of the tubular body, the shaped protrusion extends only into the exterior area of the stent graft and does not enter the inner lumen of the stent graft. The shaped protrusion may take the shape of an annular arch in this embodiment.

In another embodiment, the shaped protrusion may cross the circumference of the tubular body once to form an S-shape in cross section.

The endovascular prosthesis may also comprise either an inner reinforcement ring disposed near the fenestration around about the inner edge, or an outer reinforcement ring disposed around the outer edge or both. The rings may be concentric or eccentric. The rings may also be coincident with the circumference of the tubular wall.

The shaped protrusion may extend from the inner ring to the outer ring. The endovascular prosthesis may have more than one shaped protrusion and fenestration. The endovascular prosthesis may also have a plurality of stents disposed longitudinally along the graft material to help with sealing against a body vessel.

In a method for constructing the invention, a portion or sheet of graft material is clamped to a mold. The mold is in the shape of the shaped protrusion as described in the embodiments above. The mold can have the form of an annular arch, S-shape, or any form that creates a shaped protrusion as described above. The mold and clamped graft material is heated, thereby heat setting the graft material to conform to the mold and forming the shaped protrusion in the portion of graft material. The portion of graft material is then unclamped and separated from the mold.

In one embodiment, the shaped protrusion may be unitary with the tubular body. In this embodiment, heat is applied after clamping the mold to a sheet of graft material that is capable of being formed into a tubular shape or to a preformed tubular body.

After heat setting and removing the mold, the inner and outer ring may be attached to the graft material and a fenestration created in the inner ring.

In another embodiment, the shaped protrusion may be formed separately from the stent graft by heat setting a clamped mold and individual sheet of graft material. The formed shaped protrusion can then be excised from the sheet of graft material and then attached to another sheet of graft material, followed by the inner ring and outer ring.

The examples and description herein are illustrative and not intended to limit the present disclosure and claims. It is understood that the teachings herein may apply to use in other fields of treatment and is not limited to use in the human abdominal aorta as described.

DETAILED DESCRIPTION

Figure 1:
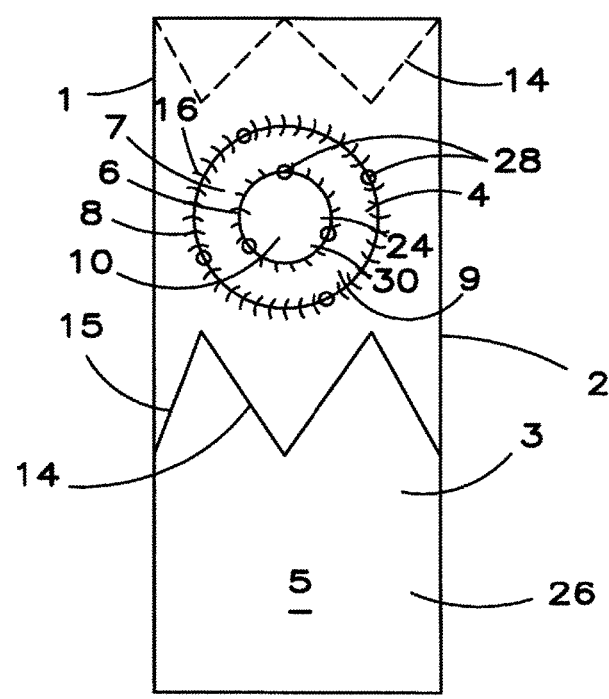
FIG. 1 is a front view of one embodiment of the present invention.
Figure 2:
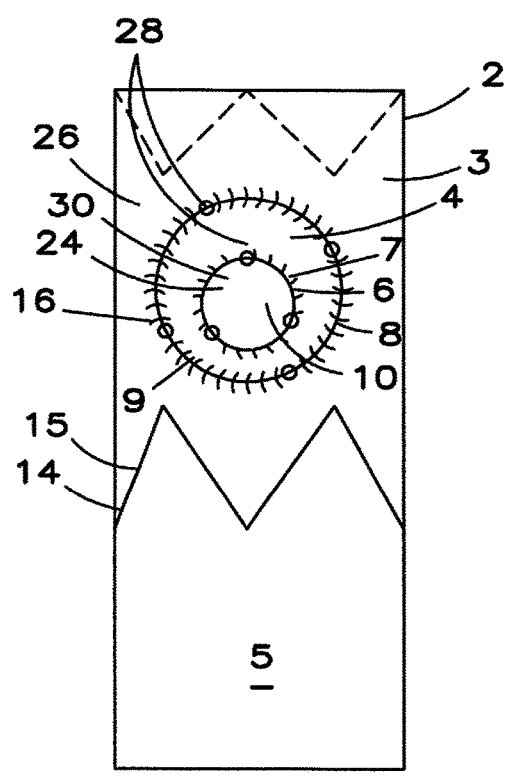
FIG. 2 is a front view of the embodiment shown in FIG. 1 after adjusting the fenestration.

Thermosetting is an irreversible curing process induced by the application of heat, chemical reaction, or irradiation. Cured material may strengthen, harden, stiffen, or become resistant to heat, corrosion, or creep. As described below, shaping a material in a mold before thermosetting allows the material to cure into a specific shape.

A preferred embodiment of a modified stent graft 2 configured for placement into a body vessel 18 according to the invention is shown in FIGS. 1-4. The stent graft 2 is formed from a flexible graft material 1 formed into a tubular body 3 along a longitudinal axis. The tubular body 3 has a longitudinal wall 5 and is open ended to allow the passage of fluids. The graft material can be any suitable graft material.

As seen in FIGS. 1-4, a series of stent rings 14 are disposed longitudinally on the inner surface 24 and the outer surface 26 of the wall 5 of the tubular body 3. The stent rings 14 may be attached to both the inner surface 24 and the outer surface 26 of the tubular body 3 to make any combination of interior and exterior stent rings 14. In an alternate embodiment, the stent rings 14 may also be wholly on the outer surface 26 or the inner surface 24 of the tubular body 3.

The stent rings 14 may be attached to the tubular body 3 by a series of stitches such as 16 as shown in FIGS. 1-4, or by any other method known in the art. A terminal stent ring 14 may be located at each end of the tubular body 3. The ends of the tubular body 3 have a diameter chosen to be sealable against a target body vessel 18.

The stent rings 14 are preferably made from a shape memory alloy, but may be made of any other suitable material including, but not limited to: stainless steel, plastic, nitinol, etc. As illustrated in FIGS. 1-4, radiopaque markers such as 28 may be attached to the rings 14 to assist with positioning or the rings themselves may be made from any suitable radiopaque material including, but not limited to, platinum or other heavy metals.

The individual struts 15 of the stent rings 14 in FIGS. 1-4 are configured in a zig-zag formation, but struts 15 may be configured in any manner suitable for use on a stent graft 2.

As illustrated in FIGS. 1-4, the invention also includes a shaped protrusion of graft material 4, an inner edge 7, and an outer edge 9 on the shaped protrusion of semi-rigid graft material 4, and a fenestration 10 within the inner edge 7. The inner edge 7 and the outer edge 9 are preferably concentric as shown, but may be eccentric in alternate embodiments.

As used in this application, the term "reinforcement ring" includes shapes that may be circular, oval, triangular, square, or any other enclosed shape.

The embodiments of FIGS. 1-4 comprise an optional inner reinforcement ring 6 about the inner edge 7 and the fenestration 10 and an outer reinforcement ring 8 about the outer edge 9. It is preferred that the inner edge 7 and outer edge 9 share boundaries with the inner reinforcement ring 6 and the outer reinforcement ring 8, respectively. Like the edges, the rings are preferably concentric, but may be eccentric. The shaped protrusion 4 is attached to the tubular wall 5 at its outer edge 9 and extends to the inner edge 7 to form the fenestration. Embodiments without reinforcement rings can be imagined, such as in FIG. 5.

In FIGS. 1-4, the reinforcement rings are attached to the outer surface 26 of tubular body 3. In alternate embodiments, the rings 6, 8 may each be located on either the inner surface 24 or outer surface 26 of the tubular body 3. The outer ring 8 is preferably disposed on or near the outer edge 9 of the shaped protrusion 4 and the inner ring is preferably disposed on or near the inner edge 7 and fenestration 10. Where the reinforcement rings 6, 8 are attached on or near the edges 7, 9 of the shaped protrusion 4, they will function similarly to the edges 7, 9 as described below; by delineating the fenestration or determining the limit of fenestration adjustability. Like the reinforcement rings 6, 8, the edges 7, 9 may be any enclosed shape.

The inner reinforcement ring 6 and the outer reinforcement ring 8 may be made of any suitable material including, but not limited to, nitinol, plastic, stainless steel, etc. The inner reinforcement ring 6 and the outer reinforcement ring 8 may alternatively be made of radiopaque material, or radiopaque markers 28 may be attached to the inner ring 6 and the outer ring 8 to assist in placement in the lumen of a body vessel 18. In a preferred embodiment both the inner ring 6 and the outer ring 8 are circular and made of nitinol.

The inner ring 6 and the outer ring 8 may be attached to the tubular body 3 via stitching 16 or any other attachment method. The inner ring 6 and the outer ring 8 may be attached to the tubular body 3 eccentrically. However, the inner ring 6 and outer ring 8 are preferably concentrically disposed so that excess graft material is equally dispersed between the inner and the outer edge 9, or the inner and the outer reinforcement ring 8. In this case there is an equal amount of graft material between any two pairs of radially synchronous points on their circumferences. The two rings are also preferably disposed on the wall 5 of the tubular body 3 so to be parallel to each other and also the curvilinear plane, or circumference, of the tubular body, such that all three are coincident or coplanar. Concentric placement of the two rings ensures the flexibility and adjustable potential of the shaped protrusion 4 and the inner ring 6 is the same in all directions. In embodiments without reinforcement rings, the inner and outer edges can be coincident with the circumference of the tubular body.

The shaped protrusion is preferably comprised of a semi-rigid material, or even more preferably, a thermoset material. The thermoset material may be any thermosettable material and is preferably a commonly used and widely commercially available biocompatible graft material such as Dacron®.

Because the shaped protrusion 4 is semi-rigid and can hold its shape, the shaped protrusion 4 does not require radial supporting structures such as a stent framework to be effective in treatment. Preferably the shaped protrusion 4 is unsupported but for an inner reinforcement ring 6 and an outer reinforcement ring 8 at or near its inner 7 and outer edges 9 respectively.

Figure 5:
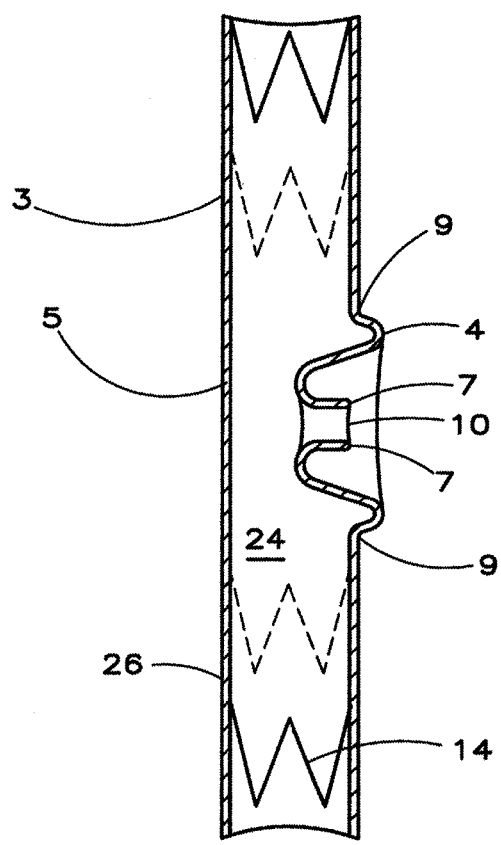
FIG. 5 is a sectional view of another embodiment of the present invention.
Figure 6:
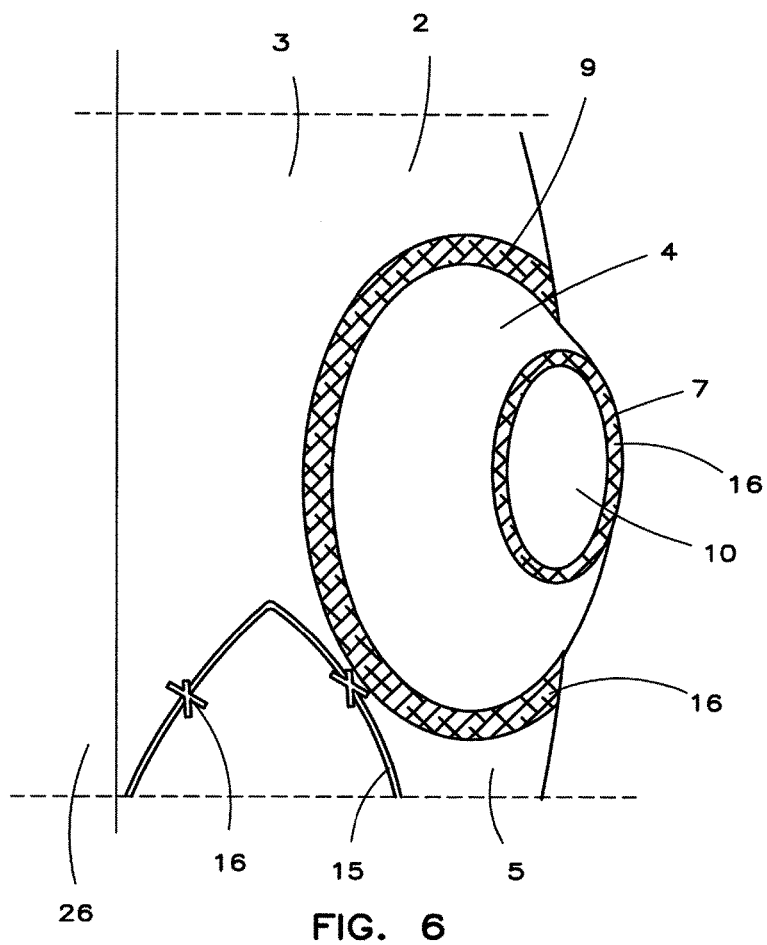
FIG. 6 is a closeup of the fenestration area of another embodiment of the current invention.

In another embodiment, the shaped protrusion 4 could have no stents and no reinforcement rings as shown in FIGS. 5-6. A featureless shaped protrusion 4 has the further advantage of reducing the profile of the stent graft 2 and the associated introducer.

The fenestration 10 is disposed within the inner edge 7 of the shaped protrusion 4. The fenestration 10 allows two-way fluid communication through the wall 5 from the exterior area 32 of the tubular body to the inner lumen 30 and vice versa. The fenestration 10 is located in the shaped protrusion 4 to form the inner edge 7. The fenestration 10 is preferably a similar diameter as the inner ring 6 and the inner edge 7 such that the inner ring 6 can be attached at the inner edge 7 to delineate the border of the fenestration 10.

As shown in FIGS. 1-4, the shaped protrusion 4 extends between the inner edge 7 and the outer edge 9 and extends from the wall 5. The shaped protrusion 4 is the area of the stent graft 2 from the inner edge 7 to the outer edge 9. The shaped protrusion 4 may be formed from a separate piece of graft material that is stitched or otherwise attached to the tubular body 3 and the inner ring 6 and the outer ring 8. However, the shaped protrusion 4 is preferably a modified section of the tubular body 3. The shaped protrusion 4 may be modified by being clamped in a mold and heat treated, such as in the molds 34 of FIGS. 7-8. When the shaped protrusion 4 is the same piece of graft material as the tubular body 3 instead of a separate piece of graft material attached to the tubular body 3, a manufacturing step and a stitch line in the stent graft 2 is eliminated.

The shaped protrusion 4 may be thermoset and can be comprised of a heat treated graft material. It is preferred that the shaped protrusion 4 be semi-rigid or become semi-rigid upon heat treating such that it can hold its shape and position in the absence of external manipulation. Furthermore, when the stent graft 2 includes reinforcement rings, the shaped protrusion 4 is semi-rigid so that it can hold its shape despite the attachment of the reinforcement rings, but also pliable enough so as to deform in response to attempted cannulation. The semi-rigidity of the ring 4 eliminates the need for a supporting structure between the inner edge 7 and the outer edge 9 and allows for a shaped protrusion free of stents. 4. A method of forming the semi-rigid shaped protrusion 4 is explained further below.

As in FIGS. 1-6, the shaped protrusion 4 preferably comprises an excess amount of graft material. That is, the area of the shaped protrusion 4 is greater than the area of an annular curvilinear plane along the wall 5 delineated by the outer edge 9 and inner edge 7 when the edges are coincident with the circumference of the wall 5. The surface area of the shaped protrusion 4 can be approximated as being greater than $(2\pi r_o^2)-(2\pi r_i^2)$, where $r_o$ is radius of the outer edge 9 and $r_i$ is radius of the inner edge 7. Where the device includes a reinforcement ring on the inner 7 or outer edge 9, the radius can be measured to or from the ring. As a result, when the shaped protrusion 4 is attached to the tubular body 3, it cannot travel linearly along the tubular plane of the stent graft 2 between the inner edge 7 and the outer edge 9. Instead, the material must follow a curved or bent path between the inner 7 and outer edge 9 to compensate for the excess graft material. The shaped protrusion 4 will therefore extend from the wall and have a protruding shape.

It is preferred that most of the shaped protrusion 4 is not in the plane of the stent graft 2 and that the shaped protrusion 4 travels from the inner edge 7 to the outer edge 9 in the exterior area 32 of the stent graft 2. In the preferred embodiment illustrated in FIGS. 1-4, the inner edge 7 and the outer edge 9 are coincident with the circumference of the tubular body 3 and the shaped protrusion 4 may form an annular arch in cross section. FIGS. 1-4 show a shaped protrusion 4 that extends radially away from the tubular body 3.

The presence of excess graft material introduces a slack in the shaped protrusion 4 between the inner edge 7 and the outer edge 9. The slack from the excess enables the inner edge 7 and fenestration to move within boundaries of the outer edge 9. In FIGS. 1-4, the inner edge 7 and the outer edge 9 are concentric and coincident with the tubular body 3. The excess material of the shaped protrusion 4 is evenly distributed in the annular area between the inner edge 7 and the outer edge 9. This allows movement equally in all directions.

As there is minimal excess graft material in the plane of the tubular body 3 between the edges, the inner edge 7 and the fenestration 10, can move in the entire area delimited by the outer edge 9 while remaining coincident with the tubular body 3 and the outer edge 9. The coincident placement of the fenestration 10, also reduces the intrusion into the stent graft inner lumen 30 by the shaped protrusion 4 and structures that may be attached to the fenestration 10, such as connecting stents.

In another embodiment shown in FIG. 6, the shaped protrusion 4 may take a dome shape, where the outer edge 9, but not the inner edge 7, is coincident with the tubular body 3. In this embodiment, the dome may advantageously evert easily because of the semi-rigidity of the shaped protrusion 4.

It is preferable that as small of an amount as possible of material be disposed in the curvilinear plane between the inner edge 7 and the outer edge 9. This enables the maximum amount of movement of the fenestration 10, and therefore maximizes the adjustability of the fenestration 10 in the inner edge 7.

Other configurations may be envisioned for the path of the shaped protrusion 4 between the inner edge 7 and the outer edge 9 which have a minimal amount of graft material in the plane of the stent graft 2 and a therefore a minimal amount of intrusion by the shaped protrusion 4 into the inner lumen 30. These embodiments still allow a very adjustable fenestration 10 and do not stray from the purpose of the invention.

For example, in the alternate embodiment of FIG. 5, the shaped protrusion 4 is disposed so as to extend from the inner lumen 30 to the exterior area 32 of the stent graft 2 by crossing the plane of the stent graft 2 once. A single portion of the shaped protrusion 4 extends radially into the inner lumen 30 of the stent graft 2 a single time. The effect of the excess graft material in the plane of the tubular body is minimal and the device retains the ability to move the inner edge 7 and adjust the fenestration 10. In this embodiment, the shaped protrusion 4 takes an S-shape in cross section and crosses the plane once.

In other embodiments, the shaped protrusion 4 may take V-shape or other similar shape in cross section. The excess surface area of the shaped protrusion 4 allows the inner edge 7 to move and adjust to fit a vessel ostium. It is preferred that the inner edge 7 is adjusted by shifting it along the plane of the tubular body 3 so that it remains coincident with the circumference of the tubular body 3. By placing the excess graft material of the shaped protrusion 4 outside of that plane, the inner ring 6 and the fenestration 10 have the maximum adjustable potential.

In an exemplary embodiment, the outer ring 8 is a circle with a diameter of 15 mm and concentric with a circular inner ring 6 having a diameter of 6 mm. In this embodiment, the fenestration 10 can be adjusted to reach a range of side branch 20 locations within 7.5 mm of the center point of the fenestration 10 from its initial, centered, position.

In alternate embodiments, the diameters of the inner ring 6 and the outer ring 8 can be altered to match and adjust to the diameter of the targeted side vessel. The closer the rings are in diameter, the less movement will be available to the inner ring 6, as there will be less free room between the rings.

Figure 3:
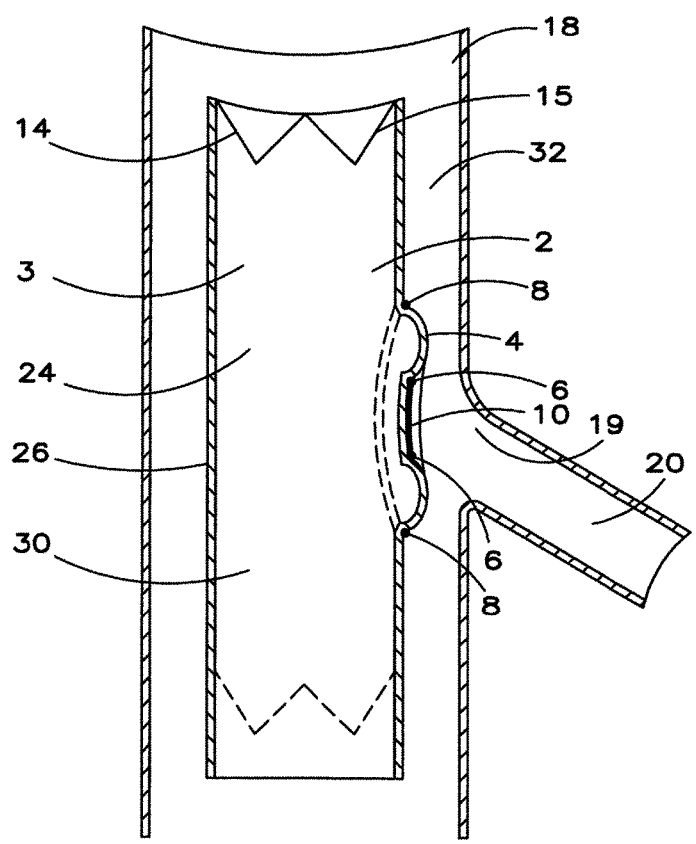
FIG. 3 shows a sectional side view of the embodiment shown in FIG. 1 located in a body vessel.
Figure 4:
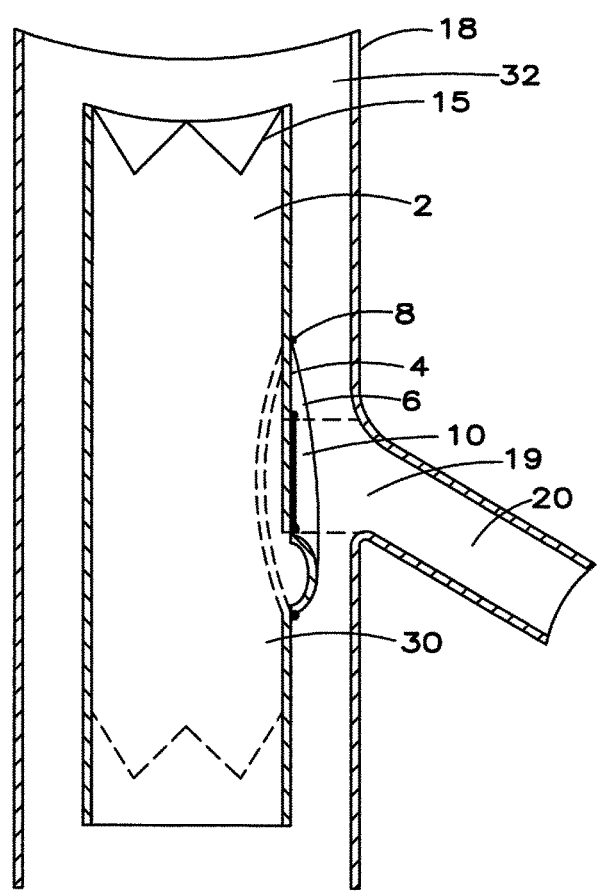
FIG. 4 shows a sectional side view of the embodiment shown in FIG. 1 located in a body lumen and after adjusting the fenestration to align with a branch vessel.

FIGS. 3-4 shows the effects of adjustment. In FIG. 3 the fenestration 10 of the stent graft 2 may not align well with the ostium 19 of the side branch vessel upon deployment in the body vessel 18. Here the ostium 19 and the fenestration are separated by distance x. However the slack from the excess graft material in the shaped protrusion 4 allows the inner ring to adjust downward, thereby aligning the fenestration 10 with the ostium 19 as in FIG. 4.

Method of Formation.

Figure 7:
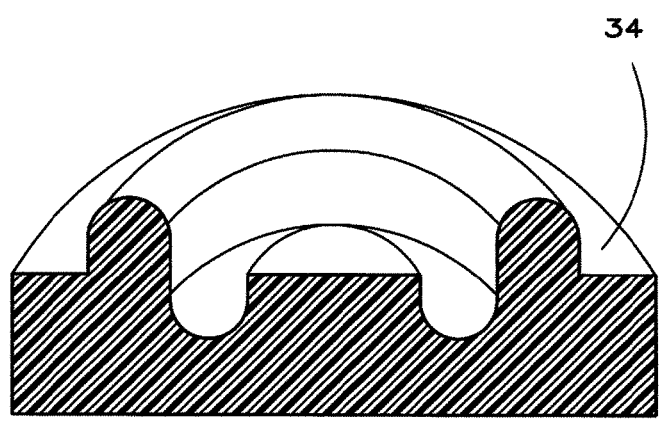
FIG. 7 is an example of a mold used to form shaped protrusion 4 in FIG. 1.
Figure 8:
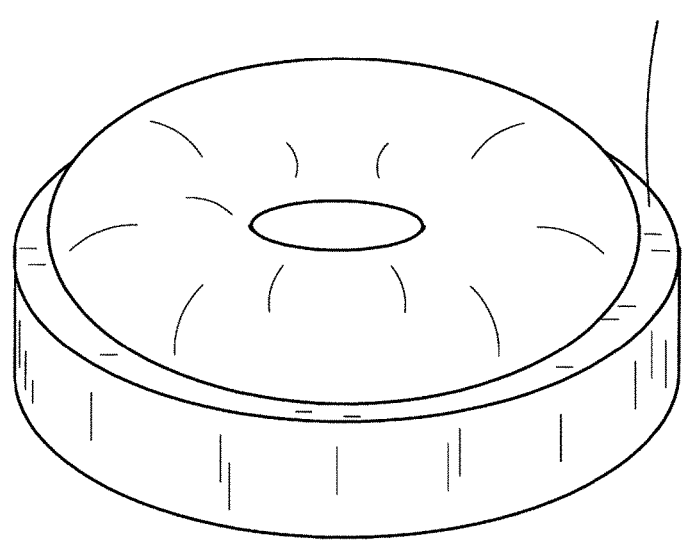
FIG. 8 is an example of a mold used to form a shaped protrusion 4 in FIG. 5.

FIGS. 7-8 depict molds 34 for two preferred embodiments of the present invention. The mold of FIG. 8 will create a shaped protrusion 4 in the shape of an annular ring, as depicted in FIGS. 1-4. The mold of FIG. 7 will create a shaped protrusion 4 having an S shape in cross section as in FIG. 5. Both embodiments of shaped protrusions may be formed through the molding process described below.

In an exemplary method of formation, the mold 34 is first clamped to either a sheet of graft material or a tube of graft material and heated. The heating process heat sets the graft material in the shape of the mold 34. The mold 34 and graft material are then unclamped creating a shaped protrusion 4.

If a tube of graft material was used, the inner ring 6 and the outer ring 8 may optionally be attached to the tube, and a fenestration 10 cut out in the inner ring 6. Stent rings 14 may be added to complete the device.

If a sheet of graft material was used, the shaped protrusion 4 can be removed from the sheet, and sewn or otherwise attached to a separate tubular body. The sheet may also be formed into a tube. The inner ring 6 and outer ring 8 can then be attached to the combined sheet and shaped protrusion 4. Stent rings 14 are then attached through methods known in the art.

The preferred method of constructing the stent graft 2 includes the steps of:
1. Clamping the mold 34 to a tubular body 3.
2. Applying heat to the clamped mold and graft material.
3. Cooling the clamped mold and graft material.
4. Removing the mold from the graft material.
5. If the mold was formed from a sheet of graft material separate from the material intended to form the main stent graft body, remove the molded shaped protrusion 4 and attach the shaped protrusion 4 to the main stent graft body.
6. Attach the inner ring 6 and outer ring 8 to the graft material.
7. Add the fenestration 10 in the graft material.

The steps describe a general method of forming a stent graft 2 of the present invention. The stent graft 2 can now be mounted onto a delivery system and delivered to the body vessel 18 in via any acceptable method.

The embodiments and figures above are merely exemplary and should not be construed as limiting the claims. It is also contemplated that minor variations may be made on the process of manufacture and the stent graft without varying from the inventive concept covered by the claims below.

What is claimed is:
1. An endovascular prosthesis comprising:
 a tubular body having a wall and comprising a graft material;
 a shaped protrusion extending from the wall and comprising a cured thermoset graft material formed into a curved shape, the shaped protrusion having an outer edge and an inner edge at least partially surrounded by the outer edge and being void of structures other than the thermoset material that extends radially between the edges; and
 a fenestration having fluid communication through the wall and disposed within the inner edge of the shaped protrusion,
 wherein the shaped protrusion is semi-rigid.
2. The endovascular prosthesis as in claim 1 wherein the shaped protrusion has a transverse length and is curved along its length.

3. The endovascular prosthesis as in claim 1 wherein the shaped protrusion has a surface area greater than a surface area of an annular curvilinear plane along the wall of the tubular body delineated by the outer edge and the inner edge of the shaped protrusion when the outer edge and the inner edge are in a position coincident with the circumference of the wall of the tubular body.

4. The endovascular prosthesis as in claim 1 wherein the shaped protrusion extends outwardly from the wall forming a dome.

5. The endovascular prosthesis as in claim 1 wherein the shaped protrusion protrudes outwardly from the prosthesis forming an arch.

6. The endovascular prosthesis as in claim 1 wherein the shaped protrusion crosses a circumference of the tubular body only once.

7. The endovascular prosthesis of claim 6 wherein the shaped protrusion forms an S-shape in cross section.

8. An endovascular prosthesis comprising:
  a tubular body having a wall and comprising a graft material;
  a shaped protrusion extending from the wall and comprising a cured thermoset material formed into a curved shape, the shaped protrusion having an outer edge and an inner edge at least partially surrounded by the outer edge and being void of structures other than the thermoset material that extend radially between the edges;
  the outer edge and the inner edge being coincident with a circumference of the tubular body; and
  a fenestration having fluid communication through the wall and disposed within the inner edge of the shaped protrusion,
  wherein the shaped protrusion is semi-rigid.

9. The endovascular prosthesis as in claim 8 wherein the shaped protrusion has a transverse length and is curved along the length.

10. The endovascular prosthesis as in claim 8 wherein the shaped protrusion crosses a circumference of the tubular body once.

11. The endovascular prosthesis as in claim 8 wherein the shaped protrusion protrudes outwardly from the prosthesis forming an arch.

12. The endovascular prosthesis as in claim 8 wherein the shaped protrusion forms an S-shape in cross section.

13. An endovascular prosthesis comprising:
  a tubular body having a wall and comprising a graft material;
  a shaped protrusion extending from the wall and comprising a cured thermoset material formed into a curved shape, the shaped protrusion having an outer edge and an inner edge at least partially surrounded by the outer edge and being void of structures other than the thermoset material that extend radially between the edges;
  the outer edge and the inner edge being coincident with the circumference of the tubular body;
  the shaped protrusion having a transverse length and being curved along its length; and
  a fenestration having fluid communication through the wall and disposed within the inner edge of the shaped protrusion,
  wherein the shaped protrusion is semi-rigid.

14. The endovascular prosthesis as in claim 13 wherein the shaped protrusion has a surface area greater than a surface area of an annular curvilinear plane along the wall of the tubular body delineated by the outer edge and the inner edge of the shaped protrusion when the outer edge and the inner edge are in a position coincident with the circumference of the wall of the tubular body.

15. The endovascular prosthesis as in claim 13 wherein an inner reinforcement ring is disposed surrounding the fenestration around about the inner edge, and an outer reinforcement ring is disposed on the wall around the outer edge.

16. The endovascular prosthesis as in claim 15 wherein the inner and outer reinforcement rings are concentric.

17. The endovascular prosthesis as in claim 15 wherein the inner and outer reinforcement rings are eccentric.

18. The endovascular prosthesis as in claim 13 wherein the tubular body and the shaped protrusion are formed from a single piece of graft material.

19. The endovascular prosthesis as in claim 13 wherein the shaped protrusion is unstitched between its edges.

* * * * *